United States Patent
Nagai et al.

(10) Patent No.: US 9,242,911 B2
(45) Date of Patent: Jan. 26, 2016

(54) PREPARATION METHOD FOR FLUORINE-CONTAINING OLEFINS HAVING ORGANIC-GROUP SUBSTITUENTS

(75) Inventors: Takabumi Nagai, Settsu (JP); Kenji Adachi, Settsu (JP); Takashi Shibanuma, Settsu (JP); Sensuke Ogoshi, Suita (JP); Masato Ohashi, Suita (JP)

(73) Assignees: OSAKA UNIVERSITY, Osaka (JP); DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 13/985,659

(22) PCT Filed: Mar. 8, 2012

(86) PCT No.: PCT/JP2012/056008
§ 371 (c)(1),
(2), (4) Date: Aug. 15, 2013

(87) PCT Pub. No.: WO2012/121345
PCT Pub. Date: Sep. 13, 2012

(65) Prior Publication Data
US 2013/0324757 A1    Dec. 5, 2013

(30) Foreign Application Priority Data

Mar. 10, 2011   (JP) .................. 2011-053625
Aug. 12, 2011   (JP) .................. 2011-177090

(51) Int. Cl.
| | |
|---|---|
| C07C 17/26 | (2006.01) |
| C07C 17/263 | (2006.01) |
| C07C 45/61 | (2006.01) |
| C07C 253/30 | (2006.01) |
| C07F 5/04 | (2006.01) |
| C07C 45/68 | (2006.01) |
| C07F 5/02 | (2006.01) |
| C07C 67/343 | (2006.01) |

(52) U.S. Cl.
CPC .............. *C07C 17/26* (2013.01); *C07C 17/263* (2013.01); *C07C 45/61* (2013.01); *C07C 45/68* (2013.01); *C07C 67/343* (2013.01); *C07C 253/30* (2013.01); *C07F 5/025* (2013.01); *C07F 5/04* (2013.01)

(58) Field of Classification Search
CPC ...... C07C 17/26; C07C 17/263; C07C 45/61; C07C 253/30; C07C 45/68; C07F 5/04
See application file for complete search history.

(56) References Cited

U.S. PATENT DOCUMENTS 5,744,635 A     4/1998   Brayer et al.
2010/0160683 A1  6/2010   Matoba et al.

FOREIGN PATENT DOCUMENTS

JP   8-508988       9/1996
JP   2010-229129   10/2010

OTHER PUBLICATIONS

Extended European Search Report issued Dec. 16, 2014 in corresponding European Application No. 12754676.0.
International Search Report issued May 29, 2012 in International (PCT) Application No. PCT/JP2012/056008.
Chen et al., "New methods for the synthesis of fluoroolefms via the palladium catalyzed cross-coupling reaction of 1-fluorovinyl halides with organoboranes and organostannanes", Journal of Fluorine Chemistry, vol. 101, 2000, pp. 285-290.
Chen et al., "Synthesis of Fluorinated Olefins via the Palladium Catalyzed Cross-Coupling Reaction of 1-Fluorovinyl Halides with Organoboranes", Tetrahedron Letters, vol. 40, 1999, pp. 827-830.
Lim et al., "Synthesis of Novel d-2-'Deoxy-2'-C-difluoromethylene-4'- thiocytidine as a Potential Antitumor Agent", Organic Letters, vol. 4, No. 4, 2002, pp. 529-531.
Drakesmith et al., "Preparation and reactions of some fluorine-containing vinyl organometallic compounds", The Journal of Organic Chemistry, vol. 33, No. 1, pp. 286-291.
Kaesz et al., "Synthesis and Cleavage of Perfluorovinyltin Compounds", Journal of the American Chemical Society, vol. 82, No. 24, 1960, pp. 6232-6235.
Martinet et al., "Preparation et reactivite de $Et_3SiCF=CFM$ (M = Li, ZnBr)", Journal of Organometallic Chemistry, vol. 367, 1989, pp. 1-10, with English abstract and cited in specification.
Dolbier et al., "Cyclization reactivities of fluorinated hex-5-enyl radicals", Journal of the Chemical Society, vol. 2, 1998, pp. 219-231.
Dixon, S., "Elimination Reaction of fluoorolefms with Organolithium Compounds", The Journal of Organic Chemistry, vol. 21, No. 4, 1956, pp. 400-403.
Huaxue Xuebao, Acta Chimica Sinica, vol. 41, No. 7, 1983, pp. 637-647, with English abstract and cited in specification.

(Continued)

*Primary Examiner* — Samantha Shterengarts
(74) *Attorney, Agent, or Firm* — Wenderoth, Lind & Ponack, L.L.P.

(57) ABSTRACT

An object of the present invention is to provide a method that enables the easy and efficient (high yield, high selectivity, low cost) preparation of a fluorine-containing olefin substituted with an organic group or groups from a fluorine-containing olefin.

[Solution]

The method for preparing a fluorine-containing olefin substituted with an organic group or groups, the method comprising a step of reacting a fluorine-containing olefin with an organic boron compound in the presence of an organic transition metal catalyst containing at least one transition metal selected from the group consisting of nickel, palladium, platinum, rhodium, ruthenium, and cobalt.

11 Claims, No Drawings

(56) References Cited

OTHER PUBLICATIONS

Aoki et al., "Synthesis and polymerization of p-pentamethyldisiloxanyl-α,β,β-trifluorost3rrene and the oxygen permeability of the polymer", Journal of Fluorine Chemistry, vol. 59, 1992, pp. 285-288.

English translation of Izvestiya Akademii Nauk SSSR, "Reactions of Phenyl Derivatives of Lanthanides with Fluoroolefms", Bulletin of the Russian Academy of Sciences Division of Chemical Sciences, No. 2, 1988, pp. 445-450.

Burdon et al., "The reactivity of the hydrofluorocarbon 1,1,1,2 -tetrafluoroethane (HFC-134a) and relaed compounds towards base attack. The generation and stability of the tetrafluoroethyl, trifluorovinyl and related anions", Journal of Fluorine Chemistry, vol. 99, 1999, pp. 127-131.

Ohashi et al., "Palladium-Catalyzed Coupling Reactions of Tetrafluoroethylene with Arylzinc Compounds", Journal of the American Chemical Society, from dx.doi.org/10.1021/ja109911p.

Yamamoto et al., "Catalytic coupling reaction of chlorotrifluoroethylene with organoboronic acids", Abstract of the Fluorine Conference of Japan, vol. 34, pp. 50-51, with English translation and cited in specification.

PREPARATION METHOD FOR FLUORINE-CONTAINING OLEFINS HAVING ORGANIC-GROUP SUBSTITUENTS

TECHNICAL FIELD

The present invention relates to a method for preparing a fluorine-containing olefin substituted with an organic group or groups.

1-Substituted fluorine-containing olefins, such as 1,1,2-trifluorostyrene, are useful for, for example, polyelectrolyte materials. Further, 1,1-disubstituted fluorine-containing olefins, such as 1,1-difluoro-2,2-diphenylethylene, are useful for, for example, medicinal products, such as enzyme inhibitors or ferroelectric materials. However, a method for easily and efficiently preparing these compounds has not been established.

For example, Non-patent Literature 1 reports that a 1,1-disubstituted fluorine-containing olefin can be prepared by a difluoromethylenation reaction through a Wittig reaction of a carbonyl compound. However, when ketone is used as a carbonyl compound, the yield is low even when an excess amount of Wittig reagent (at least 4 to 5 equivalents) is used. Further, this method also requires carcinogenic hexamethylphosphorous triamide as a phosphorous compound. As such, the method has several disadvantages.

Therefore, if it is possible to easily produce fluorine-containing olefins substituted with an organic group or groups (e.g., 1-substituted fluorine-containing olefin, 1,1-disubstituted fluorine-containing olefin, etc.) from a readily obtainable fluorine-containing olefin, such as tetrafluoroethylene (TFE), the method can be very useful as a synthetic method.

BACKGROUND ART

For example, the following methods have been reported for preparing fluorine-containing olefins substituted with organic groups.

Non-patent Literature 2 discloses a method for first converting a carbon-halogen (C—X) bond of $CF_2$=CFX (X: a halogen atom other than a fluorine atom) into a carbon-lithium (C—Li) bond by butyllithium, and then performing a C—C bond forming reaction. Non-patent Literature 3, 4 and 5 disclose a method for further converting the Li of a C—Li bond formed as described above into a metal, such as Sn, Si, or the like, and then performing a C—C bond forming reaction.

However, these methods are disadvantageous in that $CF_2$=CFX used as a raw material is relatively difficult to obtain or relatively expensive. Further, because the fluorine-containing lithium reagent having the C—Li bond formed at the first stage is very unstable, it is necessary to conduct the reaction under a low temperature of about −100° C. Therefore, these methods are not practical.

Non-patent Literature 6 to 8 disclose methods of reacting TFE with an organic lithium reagent or an organic magnesium reagent, thereby selectively substituting one fluorine atom. In the formula shown below, Ph represents an optionally substituted phenyl.

(Non-patent Literature 6)

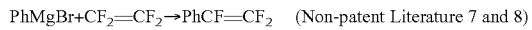

(Non-patent Literature 7 and 8)

These methods are disadvantageous in that, in order to obtain the desired product with high selectivity, it is necessary to perform the reaction at a low temperature using a large excess of raw material TFE. When the reaction temperature increases, the reaction progress goes out of control, thereby producing, in addition to the desired product, 1,2-adducts, products with a larger number of substituents, etc. Consequently, the yield of the desired product greatly decreases. When a low nucleophilic organic lanthanide reagent is used, the yield of the desired product does not improve too (Non-patent Literature 9).

Non-patent Literature 10 discloses a method of reacting HFC134a ($CF_3CFH_2$) with alkyl lithium and generating a fluorine-containing vinyl lithium by an elimination reaction. It further discloses a coupling reaction of the fluorine-containing vinyl group via a vinyl zinc reagent generated by performing a metal exchange reaction with zinc.

However, this method is disadvantageous in that it requires an excessive amount of expensive alkyl lithium, and it also poses a difficulty in precisely controlling the reaction temperature due to the instability of the fluorine-containing vinyl lithium.

If it were possible to substitute a fluorine atom (F) on an $sp^2$ hybridized carbon atom in the molecule with an organic group using TFE, hexafluoropropene (HFP), etc., which are readily obtainable industrially, in the presence of a transition metal catalyst, the method would be more useful for synthesizing substituted fluorine-containing olefins than the known methods described above.

Generally, there are many reports regarding the methods for introducing a substituent into a nonfluorinated olefin using a transition metal as a catalyst, but there are extremely few reports regarding the methods for conducting a reaction that activates a C—F bond in a fluorine-containing olefin and then generates a C—C bond. This is presumably because the binding energy of the C—F bond in the fluorine-containing olefin is much higher than that of the C—Y bond (Y represents Cl (chlorine), Br (bromine), I (iodine) or the like) of other halogen-containing olefins, and also because the fluorine atom, which is small and hard, makes it difficult to cleave the C—F bond or to perform an oxidative addition reaction of a metal with the C—F bond.

Recently, a method has been reported (Patent Literature 1 and Non-patent Literature 11) wherein the carbon-fluorine bond of tetrafluoroethylene (TFE) is activated using a transition metal catalyst to substitute fluorine with an organic group or groups using an organozinc reagent.

The advantage of this procedure is that the reaction conditions are mild compared to those in the methods described above, and the product selectivity is high. However, this method, is problematic in the handling of the organozinc reagent itself. More specifically, because organozinc reagents exhibit low stability with regard to temperature and humidity, the reaction needs to be conducted under an inert atmosphere. Furthermore, because it is difficult to store reagents for a long period of time, it is often necessary to prepare them at the time of use.

Organic boron reagents are often used in reactions where carbon-carbon bonding proceeds under the presence of a transition metal catalyst. These organic boron reagents exhibit low toxicity compared to other organic metal reagents, and the reagents per se are stable. Among them, boronate derivatives have remarkably advantageous characteristics, such as usability also in water. Due to such characteristics, boronate derivatives allow carbon-carbon bonding to be selectively formed at desired positions even in the presence of a hydroxy group, etc., which cannot coexist with other reagents having a high nucleophilicity, including the organozinc reagents mentioned above.

Organic boron reagents have various advantages as described above. However, the only reaction ever reported is a substitution reaction of a chlorine atom on an sp² hybridized carbon atom in chlorotrifluoroethylene (Non-patent Literature 12). There are no reports of the use of an organic boron reagent for a substitution reaction of a fluorine atom on an sp² hybridized carbon atom in a fluorine-containing olefin.

CITATION LIST

Patent Literature

[PTL 1] JP2010-229129A
Non-Patent Literature
[NPL 1] L. S. Jeong et al., Organic Letters, 2002, vol. 4, p. 529
[NPL 2] P. Tarrant et al., J. Org. Chem. 1968, vol. 33, p. 286
[NPL 3] F. G. A. Stone et al., J. Am. Chem. Soc., 1960, vol. 82, p. 6232
[NPL 4] J-F. Normant et al., J. Organomet. Chem. 1989, vol. 367, p. 1
[NPL 5] W. R. Dolbier, Jr. et al., J. Chem, Soc., Perkin Trans., 1998, p. 219
[NPL 6] S. Dixon, J. Org. Chem., 1956, vol. 21, p. 400
[NPL 7] J. Xikui et al., Huaxue Xuebao, 1983, vol. 41, p. 637
[NPL 8] Aoki et al., J. Fluorine Chem., 1992, vol. 59, p. 285
[NPL 9] A. B. Sigalov et al., Izvestiya Akademii Nauk SSSR, Seriya Khimicheskaya, 1988, p. 445
[NPL 10] J. Burdon et al., J. Fluorine Chem., 1999, vol. 99, p. 127
[NPL 11] S. Ogoshi et al., J. Am. Chem. Soc., doi.org/ 10.1021/jp109911p
[NPL 12] Abstract of the Fluorine Conference of Japan, vol. 34, pp. 50-51

SUMMARY OF INVENTION

Technical Problem

If the substitution reaction of a fluorine atom on an sp² hybridized carbon atom in a fluorine-containing olefin is able to proceed while taking advantage of an organic boron reagent, the preparation of fluorine-containing olefins having a great variety of substituents becomes possible.

An object of the present invention is to provide a method that allows the easy and efficient (high yield, high selectivity, and low cost) preparation of a fluorine-containing olefin substituted with an organic group or groups from a fluorine-containing olefin.

Solution to Problem

The present inventors carried out reaction of a fluorine-containing olefin, such as TFE, with an organic boron compound in the presence of a specific transition metal catalyst, and found that it was possible to prepare a fluorine-containing olefin in which a fluorine atom bonded to an sp² hybridized carbon atom is substituted with an organic group or groups of an organic magnesium reagent.

Specifically, the inventors found that by reacting TFE with a boron reagent described below in the presence of an organic nickel complex, an organic palladium complex, or the like, α,β,β-trifluorostyrene, 1,1-difluoro-2,2-diphenylethylene, or the like can be obtained. It is presumed that this reaction advances through the catalytic cycle shown in the following reaction scheme. However, the present invention is not limited to this.

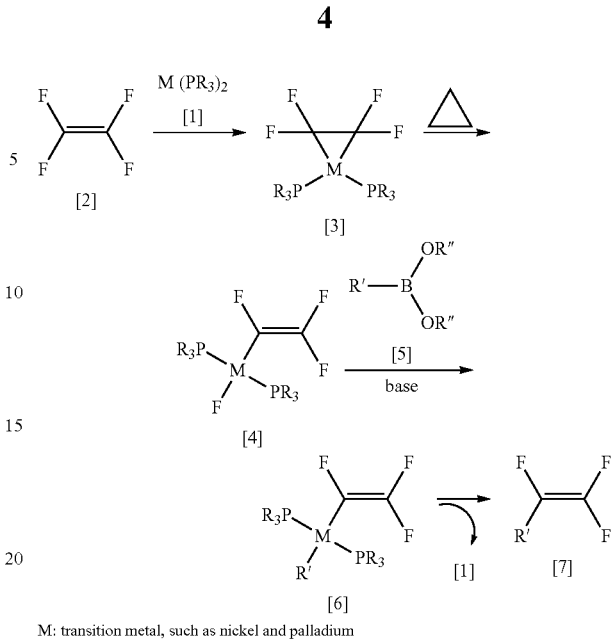

M: transition metal, such as nickel and palladium

A transition metal complex [1] is coordinated to $CF_2$=$CF_2$ [2] in a ratio of 1:1 to selectively form a complex [3]. The complex [3] is isomerized to a complex [4] by heating or by the addition of additives depending on necessity. A reaction of the complex [4] and an organic boron reagent [5] produces a novel fluorine-containing olefin [7] via a complex [6], and, at the same time, the transition metal complex [1] is reproduced to form a catalyst cycle.

The present inventors conducted extensive research based on the above finding and discovered that a fluorine-containing olefin substituted with an organic group or groups can be easily and efficiently (high yield, high selectivity, and low cost) prepared by reacting a fluorine-containing olefin with a boron compound in the presence of an organic transition metal catalyst containing a transition metal selected from the group consisting of nickel, palladium, platinum, rhodium, ruthenium, and cobalt. The present invention has thus been accomplished.

Specifically, the present invention relates to the following methods for producing a substituted fluorine-containing olefin.

Item 1.

A method for preparing a fluorine-containing olefin substituted with an organic group or groups, the method comprising a step of reacting a fluorine-containing olefin (excluding chlorotrifluoroethylene) with an organic boron compound in the presence of an organic transition metal catalyst containing at least one transition metal selected from the group consisting of nickel, palladium, platinum, rhodium, ruthenium, and cobalt.

Item 2.

The method according to Item 1, wherein the fluorine-containing olefin is an olefin substituted with one or more fluorine atoms.

Item 3.

The method according to Item 1 or 2, wherein the transition metal is at least one member selected from the group consisting of nickel and palladium.

Item 4.

The method according to any one of Items 1 to 3, wherein the organic boron compound is represented by Formula (1):

$$RBY_2 \quad (1)$$

wherein R is an optionally substituted aryl, an optionally substituted heteroaryl that is bonded via a carbon atom thereof, an optionally substituted cycloalkyl, an optionally substituted alkyl, an optionally substituted alkenyl, or an optionally substituted alkynyl;

Y is a hydroxy group, an alkoxy group, or an alkyl group; and two alkoxy or alkyl groups represented by two Ys may be crosslinked to each other; or the organic boron compound is represented by Formula (1'):

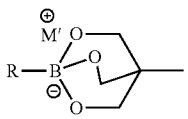

wherein M' is lithium metal, sodium metal, or potassium metal.

Item 5.

The method according to Item 4, wherein R is an optionally substituted monocyclic, bicyclic, or tricyclic aryl.

Item 6.

The method according to Item 4 or 5, wherein at least one of fluorine atoms, each of which is bonded to an $sp^2$ hybridized carbon atom of the fluorine-containing olefin, is substituted with a group represented by R.

Item 7.

The method according to any one of Items 1 to 6, wherein the step is performed in the presence of a base.

Item 8.

The method according to any one of Items 1 to 6, wherein the step is performed in the absence of a base.

Item 9.

The method according to any one of Items 1 to 7, wherein the organic transition metal catalyst is an organic nickel complex.

Item 10.

The method according to any one of Items 1 to 6 and 8, wherein the organic transition metal catalyst is an organic palladium complex.

Item 11.

The method according to any one of Items 1 to 10, wherein the fluorine-containing olefin substituted with an organic group or groups is a compound represented by Formula (2):

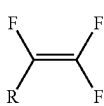

wherein R is the same as defined above.

Item 12.

A compound represented by Formula (2a):

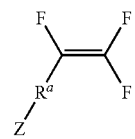

wherein $R^a$ is an optionally substituted allylene or an optionally substituted heteroallylene, Z is a group represented by Formula: $-BY_2$, wherein Y is a hydroxy group, an alkoxy group, or an alkyl group; and two alkoxy or alkyl groups represented by two Ys may be crosslinked to each other; or

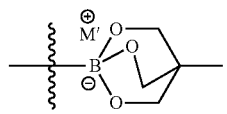

Formula wherein M' is lithium metal, sodium metal, or potassium metal.

Advantageous Effects of Invention

The preparation method of the present invention makes it possible to easily and efficiently (high yield, high selectivity, low cost) prepare a fluorine-containing olefin substituted with an organic group or groups from a fluorine-containing olefin.

DESCRIPTION OF EMBODIMENTS

The terms used in the present invention are explained below.

In this specification, "substitution" means replacing a hydrogen atom or a fluorine atom in a molecule with another atom or group.

In the specification, a "substituent" means another atom or group that replaces at least one hydrogen or fluorine atoms in a molecule.

In the specification, examples of "lower alkyl groups" (including lower alkyl moieties in substituents) include $C_{1-6}$ alkyl groups, such as methyl, ethyl, n-propyl, isopropyl, n-butyl, isobutyl, sec-butyl, tert-butyl, n-pentyl, isopentyl, neopentyl, 1-methylpentyl, n-hexyl, isohexyl, 1,1-dimethylbutyl, 2,2-dimethylbutyl, 3,3-dimethylbutyl, and the like.

In the specification, examples of "lower alkoxy groups" (including lower alkoxy moieties in substituents) include $C_{1-6}$ alkoxy groups, such as methoxy, ethoxy, n-propoxy, isopropoxy, n-butoxy, and the like.

In the specification, examples of "lower alkenyl groups" include $C_{2-6}$ alkenyl groups, such as vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, and the like.

In the specification, examples of "lower alkynyl groups" include $C_{2-6}$ alkynyl groups, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like.

In the specification, examples of "5- or 6-membered monocyclic aromatic heterocyclic rings" include 5- or 6-membered monocyclic aromatic heterocyclic rings having as the ring-constituting atoms, in addition to carbon atoms, 1 to 3 heteroatoms selected from oxygen, sulfur, and nitrogen. Specific examples of such 5- or 6-membered monocyclic aromatic heterocyclic rings include a furan ring, a thiophene ring, a pyrrole ring, an oxazole ring, an isoxazol ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, a triazine ring, and the like.

The preparation method of the present invention is explained below.

The preparation method of the present invention comprises a step of reacting fluorine-containing olefin with an organic boron compound in the presence of an organic transition metal catalyst containing a transition metal selected from nickel, palladium, platinum, rhodium, ruthenium, and cobalt. (In the specification, this step may be referred to as a reaction step.)

Examples of fluorine-containing olefins used in the present invention as a substrate include a compound which contains at least one fluorine atom bonded to the two olefin-constituting $sp^2$ hybridized carbon atoms. Chlorotrifluoroethylene is excluded from the fluorine-containing olefins used as a substrate in the present invention. The fluorine-containing olefin preferably used as a substrate in the present invention is an olefin substituted with one or more fluorine atoms. More specifically, the examples include tetrafluoroethylene (TFE), hexafluoropropylene (HFP), trifluoroethylene, 1,1-difluoroethylene (vinylidene fluoride), 1,2-difluoroethylene, and the like. In view of ready availability, versatility in fluorine chemistry, etc., TFE, trifluoroethylene, HFP, and the like are preferable.

The organic boron compound used in the preparation method of the present invention is a compound having an organic group or groups that is capable of substituting a fluorine atom on an $sp^2$ hybridized carbon atom of the fluorine-containing olefin, and the compound serves as a nucleophilic reagent.

Examples of organic groups that the organic boron compound has include optionally substituted aryl, optionally substituted heteroaryl that is bonded via a carbon atom thereof, optionally substituted cycloalkyl, optionally substituted alkyl, optionally substituted alkenyl, optionally substituted alkynyl, and the like.

The organic boron compound used in the preparation method of the present invention is preferably an organic boron compound represented by Formula (1) or Formula (1'). Each symbol in Formula (1) and Formula (1') is explained below.

Examples of aryl groups in the "optionally substituted aryl" represented by R include monocyclic, bicyclic, or tricyclic aryl groups, such as phenyl, naphthyl, anthracenyl, phenanthryl, and the like.

Examples of substituents on the alkyl include the following:
(a) halogen atom,
(b) nitro group,
(c) cyano group,
(d) amino group,
(e) carboxy group,
(f) lower alkyl group that may be optionally substituted with one or more (in particular, 1 to 3) halogen atoms,
(g) lower (in particular, $C_{2-6}$) alkenyl group,
(h) lower alkoxy group that may be optionally substituted with one or more (in particular, 1 to 3) halogen atoms,
(i) aryl group (e.g., phenyl and naphthyl),
(j) lower alkyl-sulfanyl group that may be optionally substituted with one or more (in particular, 1 to 3) halogen atoms,
(k) lower alkyl-sulfonyl group that may be optionally substituted with one or more (in particular, 1 to 3) halogen atoms,
(l) formyl group,
(m) lower alkylcarbonyl group that may be optionally substituted with one or more (in particular, 1 to 3) halogen atoms (i.e., a lower alkanoyl group),
(n) lower alkyl-carbonylamino group that may be optionally substituted with one or more (in particular, 1 to 3) halogen atoms,
(o) lower alkoxycarbonyl group that may be optionally substituted with one or more (in particular, 1 to 3) halogen atoms,
(p) —$BY_2$ wherein Y is a hydroxy group, an alkoxy group, or an alkyl group; and two alkoxy or alkyl groups represented by two Ys may be crosslinked to each other, and
(q) group:

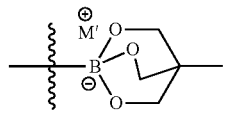

wherein M' is lithium metal, sodium metal, or potassium metal.

The aryl group may be optionally substituted with one or more (e.g., 1 to 4, in particular, 1 to 2) of the substituents described above.

Examples of heteroaryls that is bonded via a carbon atom thereof in the "optionally substituted heteroaryl that is bonded via a carbon atom thereof" represented by R include pyrrolyl (e.g., 2-pyrrolyl and 3-pyrrolyl), furyl (e.g., 2-furyl and 3-furyl), thienyl (e.g., 2-thienyl and 3-thienyl), pyrazolyl (e.g., 3-pyrazolyl and 4-pyrazolyl), imidazolyl (e.g., 2-imidazolyl and 4-imidazolyl), isoxazolyl (e.g., 3-isooxazolyl, 4-isooxazolyl, and 5-isooxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and like 5- or 6-membered monocyclic aromatic heterocyclic rings having as the ring-constituting atoms, in addition to carbon atoms, 1 to 3 heteroatoms selected from oxygen, sulfur, and nitrogen; bicyclic or tricyclic heteroaryls formed by condensation of a 5- or 6-membered monocyclic heteroaryl with one or two benzene rings; and bicyclic or tricyclic heteroaryls formed by condensation of phenyl with one or two 5- or 6-membered monocyclic aromatic heterocyclic rings.

The "carbon" in the "heteroaryl that is bonded via a carbon atom thereof" means carbon atoms constituting "heteroaryl."

Examples of substituents on the heteroaryl include:
(a) halogen atom,
(b) nitro group,
(c) cyano group,
(d) amino group,

9

(e) carboxy group,
(f) lower alkyl group that may be optionally substituted with one or more (in particular, 1 to 3) halogen atoms,
(g) lower (in particular, $C_{2-6}$) alkenyl group,
(h) lower alkoxy group that may be optionally substituted with one or more (in particular, 1 to 3) halogen atoms,
(i) aryl group (e.g., phenyl and naphthyl),
(j) lower alkyl-sulfanyl group that may be optionally substituted with one or more (in particular, 1 to 3) halogen atoms,
(k) lower alkyl-sulfonyl group that may be optionally substituted with one or more (in particular, 1 to 3) halogen atoms,
(l) formyl group,
(m) lower alkylcarbonyl group that may be optionally substituted with one or more (in particular, 1 to 3) halogen atoms (i.e., a lower alkanoyl group),
(n) lower alkyl-carbonylamino group that may be optionally substituted with one or more (in particular, 1 to 3) halogen atoms,
(o) lower alkoxycarbonyl group that may be optionally substituted with one or more (in particular, 1 to 3) halogen atoms,
(p) —$BY_2$ wherein Y is a hydroxy group, an alkoxy group, or an alkyl group; and two alkoxy or alkyl groups represented by two Ys may be crosslinked to each other, and
(q) a group represented by the formula:

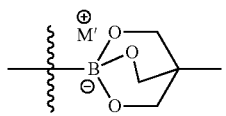

the heteroaryl may be optionally substituted with one or more (e.g., 1 to 4, in particular, 1 to 2) of the substituents described above.

Examples of cycloalkyl groups of the "optionally substituted cycloalkyl" represented by R include $C_{3-6}$ cycloalkyl groups, such as cyclopropyl, cyclobutyl, cyclopentyl, cyclohexyl, and the like.

Examples of substituents on the cycloalkyl include:
(a) halogen atom,
(b) nitro group,
(c) cyano group,
(d) amino group,
(e) carboxy group,
(f) lower alkyl group that may be optionally substituted with one or more (in particular, 1 to 3) halogen atoms,
(g) lower (in particular, $C_{2-6}$) alkenyl group,
(h) lower alkoxy group that may be optionally substituted with one or more (in particular, 1 to 3) halogen atoms,
(i) aryl group (e.g., phenyl and naphthyl),
(j) lower alkyl-sulfanyl group that may be optionally substituted with one or more (in particular, 1 to 3) halogen atoms,
(k) lower alkyl-sulfonyl group that may be optionally substituted with one or more (in particular, 1 to 3) halogen atoms,
(l) formyl group,
(m) lower alkylcarbonyl group that may be optionally substituted with one or more (in particular, 1 to 3) halogen atoms (i.e., a lower alkanoyl group),
(n) lower alkyl-carbonylamino group that may be optionally substituted with one or more (in particular, 1 to 3) halogen atoms, and
(o) lower alkoxycarbonyl group that may be optionally substituted with one or more (in particular, 1 to 3) halogen atoms.

10

The cycloalkyl may be optionally substituted with one or more (e.g., 1 to 4, in particular, 1 to 2) of the substituents described above.

Examples of alkyl groups of the "optionally substituted alkyl" represented by R include lower alkyl groups.

Examples of substituents on the alkyl include:
(a) halogen atom,
(b) nitro group,
(c) cyano group,
(d) amino group,
(e) carboxy group,
(f) lower alkoxy group that may be optionally substituted with one or more (in particular, 1 to 3) halogen atoms,
(g) aryl group (e.g., phenyl and naphthyl),
(h) lower alkyl-sulfanyl group that may be optionally substituted with one or more (in particular, 1 to 3) halogen atoms,
(i) lower alkyl-sulfonyl group that may be optionally substituted with one or more (in particular, 1 to 3) halogen atoms,
(j) formyl group,
(k) lower alkylcarbonyl group that may be optionally substituted with one or more (in particular, 1 to 3) halogen atoms (i.e., lower alkanoyl groups),
(l) lower alkyl-carbonylamino group that may be optionally substituted with one or more (in particular, 1 to 3) halogen atoms, and
(m) lower alkoxycarbonyl group that may be optionally substituted with one or more (in particular, 1 to 3) halogen atoms.

The alkyl group may be optionally substituted with one or more (for example, 1 to 3, in particular, 1 to 2) of the substituents described above.

Examples of alkenyl groups of the "optionally substituted alkenyl" represented by R include lower alkenyl groups.

Examples of substituents on the alkenyl include:
(a) halogen atom,
(b) nitro group,
(c) cyano group,
(d) amino group,
(e) carboxy group,
(f) lower alkyl group that may be optionally substituted with one or more (in particular, 1 to 3) halogen atoms,
(g) lower (in particular, $C_{2-6}$) alkenyl group,
(h) lower alkoxy group that may be optionally substituted with one or more (in particular, 1 to 3) halogen atoms,
(i) aryl group (e.g., phenyl and naphthyl),
(j) lower alkyl-sulfanyl group that may be optionally substituted with one or more (in particular, 1 to 3) halogen atoms,
(k) lower alkyl-sulfonyl group that may be optionally substituted with one or more (in particular, 1 to 3) halogen atoms,
(l) formyl group,
(m) lower alkylcarbonyl group that may be optionally substituted with one or more (in particular, 1 to 3) halogen atoms (i.e., a lower alkanoyl group),
(n) lower alkyl-carbonylamino group that may be optionally substituted with one or more (in particular, 1 to 3) halogen atoms, and
(o) lower alkoxycarbonyl group that may be optionally substituted with one or more (in particular, 1 to 3) halogen atoms.

The alkenyl may be optionally substituted with one or more (for example, 1 to 3, in particular, 1 to 2) of the substituents described above.

Examples of alkynyl group of the "optionally substituted alkynyl" represented by R include lower alkynyl groups.

Examples of substituents on the alkynyl include:
(a) halogen atom,
(b) nitro group, (c) cyano group, (d) amino group, (e) carboxy group, (f) lower alkoxy group that may be optionally substituted with one or more (in particular, 1 to 3) halogen atoms, (g) aryl group (e.g., phenyl and naphthyl), (h) lower alkyl-sulfanyl group that may be optionally substituted with one or more (in particular, 1 to 3) halogen atoms, (i) lower alkyl-sulfonyl group that may be optionally substituted with one or more (in particular, 1 to 3) halogen atoms, (j) formyl group, (k) lower alkylcarbonyl group that may be optionally substituted with one or more (in particular, 1 to 3) halogen atoms (i.e., lower alkanoyl groups), (l) lower alkyl-carbonylamino group that may be optionally substituted with one or more (in particular, 1 to 3) halogen atoms, and (m) lower alkoxycarbonyl group that may be optionally substituted with one or more (in particular, 1 to 3) halogen atoms.

The alkynyl may be optionally substituted with one or more (for example, 1 to 3, in particular, 1 to 2) of the substituents described above.

R is, preferably, an optionally substituted monocyclic, bicyclic, or tricyclic aryl, and more preferably phenyl.

Examples of "alkoxy groups" represented by Y include lower alkoxy groups.

Examples of "alkyl groups" represented by Y include lower alkyl groups.

When two Ys are hydroxy groups, the organic boron compound used in the present invention is boronic acid.

When two alkoxy groups represented by Y are cross-linked to each other, the organic boron compound used in the present invention is boronate ester.

In this case, the portion represented by $BY_2$ in Formula (1) is:

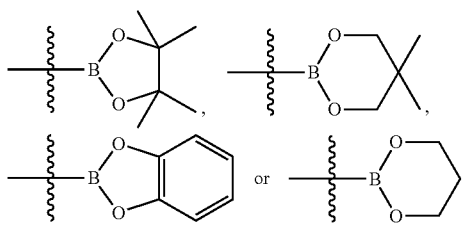

When two alkyl groups represented by Y are cross-linked to each other, examples of the portion represented by $BY_2$ in Formula (1) include groups having a bicyclo structure such as 9-borabicyclo[3.3.1]nonane whose structure is shown below.

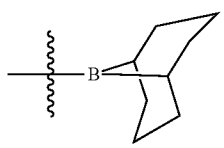 [SMILES: *B1C2CCCC1CCC2]

Preferable examples of the portion represented by $BY_2$ in Formula (1) are shown below.

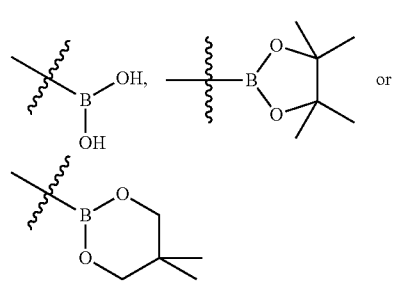

[Chem. 10]

Preferable examples of organic boron compounds used in the present invention include 5,5-dimethyl-2-phenyl-1,3,2-dioxaborinane, phenylboronic acid pinacol ester, phenylboronic acid, 2-naphthylboronic acid, 5,5-dimethyl-2-phenyl-1,3,2-dioxaborinane, 5,5-dimethyl-2-[4-(trifluoromethyl)phenyl]-1,3,2-dioxaborinane, 5,5-dimethyl-2-(4-formyl)phenyl-1,3,2-dioxaborinane, 1,4-bis-(5,5-dimethyl-1,3,2-dioxaborinane-2-yl)benzene, 5,5-dimethyl-2-(4-methoxycarbonyl)phenyl-1,3,2-dioxaborinane, 5,5-dimethyl-2-(4-cyano)phenyl-1,3,2-dioxaborinane, and 2-(5,5-dimethyl-1,3,2-dioxaborinane-2-yl)toluene.

The amounts of the fluorine-containing olefin and the organic boron compound may be appropriately determined according to the number of fluorine atoms subjected to substitution reaction in the fluorine-containing olefin. The amount of fluorine-containing olefin is generally about 0.1 to 100 mol, and preferably about 0.5 to 10 mol, per mol of the organic boron compound.

The organic transition metal catalyst used in the present invention is an organic transition metal catalyst containing a transition metal selected from nickel, palladium, platinum, rhodium, ruthenium, and cobalt. The transition metal is preferably selected from nickel and palladium. The organic transition metal catalyst containing a transition metal selected from nickel and palladium is specifically an organic nickel complex or an organic palladium complex.

The nickel complexes and palladium complexes include those added as reagents and those generated as reaction products.

Examples of palladium complexes include zerovalent palladium complexes, zerovalent palladium complexes produced from divalent palladium complexes during reaction, and complexes obtained by mixing these complexes with at least one compound (ligand) selected from the group consisting of diketone, phosphine, diamine and bipyridyl.

Zerovalent palladium complexes are not limited, and examples thereof include $Pd_2(dba)_3$ (dba represents dibenzylideneacetone), $Pd(COD)_2$ (COD represents cycloocta-1,5-diene), Pd(DPPE) (DPPE represents 1,2-bisdiphenylphosphinoethane), $Pd(PCy_3)_2$ (Cy represents a cyclohexyl group), $Pd(Pt\text{-}Bu_3)_2$ (t-Bu represents a t-butyl group), $Pd(PPh_3)_4$ (Ph represents a phenyl group), and the like.

Examples of divalent palladium complexes include palladium chloride, palladium bromide, palladium acetate, bis(acetylacetonato)palladium(II), dichloro($\eta^4$-1,5-cyclooctadiene)palladium(II), and complexes in which a phosphine ligand, such as triphenylphosphine, is coordinated to these palladium complexes. These divalent palladium complexes are reduced, for example, by a co-existing reduction species (phosphine, zinc, organometallic reagent, etc.) during reaction, thereby producing zerovalent palladium complexes.

The aforementioned zerovalent palladium complexes and zerovalent palladium complexes produced by reduction from divalent palladium complexes during reaction may be converted into zerovalent palladium complexes that are involved in reaction by acting on a compound (ligand), such as diketone, phosphine, diamine, or bipyridyl, that is added during the reaction as necessary. The number of ligands coordinated to a zerovalent palladium complex during reaction is not necessarily known.

Using the above ligands, these palladium complexes are often formed into a homogeneous solution with a reaction substrate to be used in the reaction. In addition, these palladium complexes may be used as a heterogeneous catalyst dispersed or supported in a polymer, such as polystyrene or polyethylene. Such a heterogeneous catalyst is advantageous in the process of catalyst recovery, etc. Specific examples of the catalytic structure, as shown in the chemical formula below, include a structure wherein a metal atom is fixed by polymer phosphine that is formed by introducing phosphine into cross-linked polystyrene (PS) chains or the like. Other than the one described above, polymer phosphines disclosed in the following documents may be used.
1) Kanbara et al., Macromolecules, vol. 33, p. 657 (2000)
2) Yamamoto et al., J. Polym. Sci., vol. 40, p. 2637 (2002),
3) JP06-32763A
4) JP2005-281454A
5) JP2009-527352A

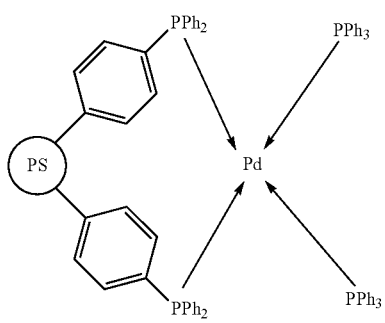

wherein PS represents polystyrene and Ph represents phenyl.

Examples of diketones include β-diketones, such as acetylacetone, 1-phenyl-1,3-butanedione, 1,3-diphenylpropanedion, and the like.

Preferable examples of phosphines include trialkylphosphines and triarylphosphines. Examples of trialkylphosphines include tri($C_{3-20}$ alkyl)phosphines, such as tricyclohexylphosphine, triisopropylphosphine, tri-t-butylphosphine, trihexylphosphine, triadamantyiphosphine, tricyclopentylphosphine, di-t-butylmethylphosphine, tribicyclo[2,2,2]octylphosphine, trinorbornylphosphine, and the like. Examples of triarylphosphines include tri(monocyclic aryl)phosphines, such as triphenylphosphine, trimesitylphosphine, tri(o-tolyl)phosphine, and the like. Among these, triphenylphosphine, tricyclohexylphosphine, and tri-t-butylphosphine are preferable. Additionally, bidentate ligands such as 1,4-bis(diphenylphosphino)butane, 1,3-bis(diphenylphosphino)propane, and 1,1'-bis(diphenylphosphino)ferrocene may also be used.

As described above, aryl phosphine for use in a heterogeneous catalyst wherein phosphine units are introduced into polymer chains may also be preferably used. A specific example is triaryl phosphine, shown in the formula below, wherein one phenyl in triphenyl phosphine is bonded to a polymer chain.

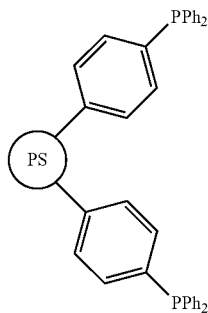

wherein PS represents polystyrene and Ph represents phenyl.

Examples of diamines include tetramethylethylenediamine, 1,2-diphenylethylenediamine, and the like.

Among these ligands, phosphine, diamine, and bipyridyl are preferable. Triarylphosphine is more preferable. Triphenylphosphine is particularly preferable. Generally, it is possible to more efficiently obtain the target substituted fluorine-containing olefin by using a palladium complex having a bulky ligand, such as phosphine.

Examples of nickel complexes include zerovalent nickel complexes, zerovalent nickel complexes produced from divalent nickel complexes during reaction, and complexes obtained by mixing these complexes with at least one compound (ligand) selected from the group consisting of diketone, phosphine, diamine and bipyridyl.

Zerovalent nickel complexes are not limited, and examples thereof include $Ni(COD)_2$, $Ni(CDD)_2$ (CDD represents cyclodeca-1,5-diene), $Ni(CDT)_2$ (CDT represents cyclodeca-1,5,9-triene), $Ni(VCH)_2$ (VCH represents 4-vinyl cyclohexene), $Ni(CO)_4$, $(PCy_3)_2Ni\!-\!N\!\equiv\!N\!-\!Ni(PCy_3)_2$, $Ni(PPh_3)_4$, and the like.

Examples of divalent nickel complexes include nickel chloride, nickel bromide, nickel acetate, bis(acetylacetonato) nickel(II), and complexes in which a phosphine ligand, such as triphenylphosphine, is coordinated to these nickel complexes. These divalent nickel complexes are reduced, for example, by a co-existing reduction species (phosphine, zinc, organometallic reagent, etc.) during reaction, thereby producing zerovalent nickel complexes.

The aforementioned zerovalent nickel complexes and zerovalent nickel complexes produced by reduction from divalent nickel complexes during reaction may be converted into zerovalent nickel complexes that are involved in reaction by acting on the ligand added during the reaction as necessary. The number of ligands coordinated to a zerovalent nickel complex during reaction is not necessarily known. The nickel complexes preferably have a high capability to stabilize the zerovalent nickel complex produced in the system. Preferable examples thereof include complexes having phosphine, diamine, bipyridyl, in particular, phosphine, or the like, as a ligand.

Preferable examples of phosphines include trialkylphosphines and triarylphosphines. Examples of trialkylphosphines include tri($C_{3-20}$ alkyl)phosphines, such as tricyclohexylphosphine, triisopropylphosphine, tri-t-butylphosphine, trihexylphosphine, triadamantyiphosphine, tricyclopentylphosphine, di-t-butylmethylphosphine, tribicyclo[2,2,2]octylphosphine, trinorbornylphosphine, and the like. Examples of triarylphosphines include tri(monocyclic aryl)phosphines, such as triphenylphosphine, trimesitylphosphine, tri(o-tolyl)phosphine, and the like. Among these, triphenylphosphine, tricyclohexylphosphine, tri-t-butylphosphine, and triisopropylphosphine are preferable.

Furthermore, as described above, aryl phosphine for use in a heterogeneous catalyst wherein phosphine units are introduced into polymer chains may also preferably be used. A specific example is triaryl phosphine, wherein, as shown in the chemical formula below, one phenyl of triphenyl phosphine is introduced into a polymer chain.

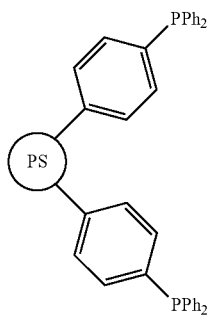

wherein PS represents polystyrene and Ph represents phenyl.

Examples of diamines include tetramethylethylenediamine, 1,2-diphenylethylenediamine, and the like.

Among these ligands, bulky ligands, such as triarylphosphines including triphenylphosphine, tri(o-tolyl)phosphine, and the like; tricyclohexylphosphine; tri-t-butylphosphine; and the like are preferable. Generally, it is possible to more efficiently obtain the target substituted fluorine-containing olefin by using a nickel complex having a bulky ligand, such as triaryl phosphine.

Among these organic transition metal catalysts, organic nickel complexes are preferable in terms of the yield, selectivity, and the like of the target fluorine-containing olefin substituted with an organic group or groups.

The amount of the organic transition metal catalyst used is not particularly limited. However, the amount thereof is generally about 0.0001 to 1 mol, preferably about 0.001 to 0.2 mol, per mol of the organic boron compound.

When a ligand is added, the amount of the ligand is generally about 0.0002 to 2 mol, preferably about 0.02 to 0.4 mol, per mol of the organic boron compound. The molar ratio of the ligand to the catalyst is generally 2/1 to 10/1, and preferably 2/1 to 4/1.

The reaction process is preferably performed in the presence of a base. Examples of bases include hydroxides, such as lithium hydroxide, sodium hydroxide, potassium hydroxide, magnesium hydroxide, and calcium hydroxide; carbonate compounds, such as lithium carbonate, sodium carbonate, sodium hydrogen carbonate, potassium carbonate, potassium hydrogen carbonate, magnesium carbonate, calcium carbonate, barium carbonate, and cesium carbonate; phosphate compounds, such as lithium phosphate, sodium phosphate, and potassium phosphate; acetate compounds, such as lithium acetate, sodium acetate, magnesium acetate, calcium acetate; and alkoxides, such as lithium methoxide, lithium-t-butoxide, sodium methoxide, sodium-t-butoxide, and potassium-t-butoxide; and the like.

However, when the organic transition metal catalyst is an organic palladium complex, the reaction satisfactorily proceeds without external addition of a base.

This is presumably due to the following mechanism:

The binding energy of the Pd—F bond is relatively low; therefore, fluorine easily liberates from the intermediate [4] in the reaction scheme showing the catalytic cycle. The fluorine liberated here serves as a base and is capable of activating an organic boron reagent. In the transmetalation process from the intermediate [4] to the intermediate [6], addition of a Lewis acidic additive can accelerate the process. In this process, the boron atom of the organic boron reagent (the compound shown by Formula (1) and the compound shown by Formula (1')) can function as a Lewis acid. For the reason described above, in the present invention, the need to add a Lewis acidic or basic reagent to the reaction system is lower than that in the prior art (Patent Literature 1), which relates to a substitution reaction of fluorine-containing olefin. Here, the fact that only a small number of compounds need to be added to the reaction system is very advantageous in light of the efficiency of the production process.

However, the present invention is not limited to such a presumed mechanism.

As described above, the reaction process is preferably conducted in the absence of a metallic halogenation reagent, (e.g., salts whose conjugated cations are Lewis acidic; for example, lithium salts, such as lithium chloride, lithium bromide and lithium iodide, and magnesium salts, such as magnesium bromide and magnesium iodide).

The "absence" condition does not have to be complete absence; a substantial absence may serve the purpose.

The amount of the base is generally 0.1 to 10 mol and preferably 0.1 to 5 mol per mole of organic boron compound.

Generally, the reaction is performed using a base in an amount at least equivalent to the organic boron compound to convert the boron into borate (activator).

The reaction temperature is not particularly limited. Generally, the reaction temperature is −100 to 200° C., preferably 0 to 150° C., more preferably room temperature (about 20° C.) to 100° C., still more preferably 30 to 100° C., particularly preferably 50 to 100° C., and most preferably 70 to 100° C. The reaction process of the present invention is preferably conducted under heating. The term "under heating" means employing temperature conditions higher than room temperature (about 20° C.), and more specifically, the reaction temperature is 30° C. or higher. Because the trifluorovinyl derivative, i.e., the reaction product, may dimerize under a high temperature, the upper limit of the reaction temperature may be determined to be less than the temperature causing dimerization.

Although the reaction time is not particularly limited, the lower limit thereof may be, for example, about 10 minutes, 2 hours, 5 hours, or 3 hours, and the upper limit thereof may be for about 15 days, about 7 days, about 72 hours, or about 50 hours.

Although it is not particularly limited, the reaction is generally performed in the presence of an inactive gas, such as argon or nitrogen, considering the activity of the organic transition metal catalyst. Further, the reaction may be performed under increased pressure, atmospheric pressure, or decreased pressure. Generally, the reaction is preferably performed under increased pressure, i.e., at about 0.1 to 10 MPa, and more preferably about 0.1 to 1 MPa.

The reaction process of the present invention is preferably conducted in a solvent. The solvent to be used is not limited insofar as it does not adversely affect the reaction. Examples thereof include aromatic hydrocarbon solvents, such as benzene, toluene, and xylene; aliphatic hydrocarbon solvents, such as hexane and cyclohexane; ether solvents, such as tetrahydrofuran (THF), dioxane, diethyl ether, glyme, and diglyme; and nitrile solvents, such as acetonitrile, propionitrile, dimethylcyanamide, and t-butylnitrile; and the like. Of these, ether solvents, such as dioxane and THF, are preferable.

The fluorine-containing olefin substituted with an organic group or groups thus obtained is preferably, for example, a compound represented by Formula (2):

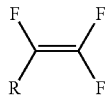

(2)

wherein R is the same as defined above.

Among the fluorine-containing olefins substituted with an organic group or groups, the following compounds are novel. One is shown in Formula (2a) below.

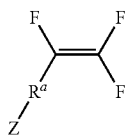

(2a)

wherein $R^a$ is an optionally substituted allylene or an optionally substituted heteroallylene, Z is a group represented by Formula: —$BY_2$ wherein Y is a hydroxy, alkoxy or alkyl; the two alkoxy or alkyl groups represented by two Ys may be crosslinked to each other.

Another novel compound is shown below.

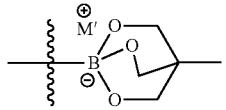

The optionally substituted allylene represented by $R^a$ is a divalent group formed by removing one hydrogen atom from on a ring-constituting atom of the "aryl group" in the "optionally substituted aryl" represented by R.

The "optionally substituted heteroallylene" represented by $R^a$ is a divalent group formed by removing one hydrogen atom on a ring-constituting atom of the "heteroaryl" in the "optionally substituted heteroaryl" represented by R.

One example of the compound represented by Formula (2a) is 5,5-dimethyl-2-(4-(1,2,2-trifluorovinyl)phenyl)-1,3,2-dioxaborinane.

The substituted fluorine-containing olefin obtained by the reaction process described above may be purified by a known purification method, such as distillation.

The thus-obtained substituted fluorine-containing olefin is useful for, for example, fluorocarbon rubber, materials for antireflection membrane, ion-exchange membranes, fuel-cell electrolyte membrane, liquid crystal materials, materials for piezoelectric elements, enzyme inhibitors, materials for insecticides, and the like.

EXAMPLES

The present invention is described below with reference to Examples; these Examples, however, do not limit the scope of the invention.

The abbreviations used in the Examples are as follows.
cod: cyclooctadiene
Cy: cyclohexyl
TFE: tetrafluoroethylene
THF: tetrahydrofuran
PhMgBr: phenyl magnesium bromide
dba: dibenzylideneacetone Example 1

In a glove box, a dioxane (0.4 mL)-THF-$d_8$ (0.1 mL) solution of Ni(cod)$_2$ (2.8 mg, 0.01 mmol), PCy$_3$ (5.6 mg, 0.02 mmol), 5,5-dimethyl-2-phenyl-1,3,2-dioxaborinane (19.0 mg, 0.1 mmol), and cesium carbonate (35.8 mg, 0.11 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. The resulting reaction solution was allowed to stand at 100° C. for 16 hours. The reaction was monitored by $^{19}$F-NMR. Based on the internal standard, it was confirmed that α,β,β-trifluorostyrene was obtained at a yield of 49%.

α,β,β-Trifluorostyrene:
$^{19}$F-NMR (THF-$d_8$, δ/PPm): −179.0 (dd, $J_{FF}$=32.7, 110.3 Hz, 1F, F$^1$), −118.5 (dd, $J_{FF}$=73.5, 110.3 Hz, 1F, F$^3$), −104.2 (dd, $J_{FF}$=32.7, 73.5 Hz, 1F, F$^2$).

Example 2

In a glove box, a THF (0.4 mL)-C$_6$D$_6$ (0.1 mL) solution of Ni(cod)$_2$ (2.8 mg, 0.01 mmol), PCy$_3$ (5.6 mg, 0.02 mmol), 5,5-dimethyl-2-phenyl-1,3,2-dioxaborinane (19.0 mg, 0.1 mmol), and cesium carbonate (35.8 mg, 0.11 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 16 hours. The reaction was monitored by $^{19}$F-NMR. Based on the internal standard, it was confirmed that α,β,β-trifluorostyrene was obtained at a yield of 41%, 1,1-difluoro-2,2-diphenylethylene was obtained at a yield of 1%, and 1,2-difluoro-1,2-diphenylethylene was obtained at a yield of 3%.

α,β,β-Trifluorostyrene:
$^1$H-NMR (C$_6$D$_6$): δ 7.16 (tt, J=7.5, 1.5 Hz, 1H), 7.47 (dd, J=8.5, 7.5 Hz, 2H), 7.59 (dd, J=8.5, 1.5 Hz, 2H).
$^{19}$F-NMR (C$_6$D$_6$): δ −103.5 (dd, J=72, 32 Hz, 1F), −118.0 (dd, J=72, 107 Hz, 1F), −179.2 (dd, J=107, 32 Hz, 1F).

1,1-Difluoro-2,2-diphenylethylene:
$^{19}$F-NMR (C$_6$D$_6$): δ −91.5 (s). MS m/z 216 (M$^+$), 166 (M-CF$_2$), 50 (CF$_2$).

1,2-Difluoro-1,2-diphenylethylene:
$^{19}$F-NMR (C$_6$D$_6$): δ trans isomer −154.8 (s), cis isomer −130.5 (s).

Example 3

In a glove box, a THF (0.4 mL)-C$_6$D$_6$ (0.1 mL) solution of Ni(cod)$_2$ (2.8 mg, 0.01 mmol), PCy$_3$ (5.6 mg, 0.02 mmol), 5,5-dimethyl-2-phenyl-1,3,2-dioxaborinane (19.0 mg, 0.1 mmol), and sodium carbonate (42.4 mg, 0.4 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35

MPa) was further added thereto. This reaction solution was allowed to stand at 100° C. for 16 hours. The reaction was monitored by $^{19}$F-NMR. Based on the internal standard, it was confirmed that α,β,β-trifluorostyrene was obtained at a yield of 7%.

Example 4

In a glove box, a THF (0.4 mL)-C$_6$D$_6$ (0.1 mL) solution of Ni(cod)$_2$ (2.8 mg, 0.01 mmol), PCy$_3$ (5.6 mg, 0.02 mmol), 5,5-dimethyl-2-phenyl-1,3,2-dioxaborinane (19.0 mg, 0.1 mmol), and potassium carbonate (55.3 mg, 0.4 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 16 hours. The reaction was monitored by $^{19}$F-NMR. Based on the internal standard, it was confirmed that α,β,β-trifluorostyrene was obtained at a yield of 26%, and 1,2-difluoro-1,2-diphenylethylene was obtained at a yield of 1%.

Example 5

In a glove box, a THF (0.4 mL)-C$_6$D$_6$ (0.1 mL) solution of Ni(cod)$_2$ (2.8 mg, 0.01 mmol), PCy$_3$ (5.6 mg, 0.02 mmol), 5,5-dimethyl-2-phenyl-1,3,2-dioxaborinane (19.0 mg, 0.1 mmol), and potassium-t-butoxide (44.9 mg, 0.4 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 16 hours. The reaction was monitored by $^{19}$F-NMR. Based on the internal standard, it was confirmed that α,β,β-trifluorostyrene was obtained at a yield of 17%, 1,1-difluoro-2,2-diphenylethylene was obtained at a yield of 2%, and 1,2-difluoro-1,2-diphenylethylene was obtained at a yield of 2%.

Example 6

In a glove box, a THF (0.4 mL)/C$_6$D$_6$ (0.1 mL) solution of Pd$_2$(dba)$_3$ (5 mg, 0.005 mmol), PPh$_3$ (5.3 mg, 0.02 mmol), 5,5-dimethyl-2-phenyl-1,3,2-dioxaborinane (19.0 mg, 0.1 mmol), potassium iodide (32.1 mg, 0.240 mmol), and cesium carbonate (39.1 mg, 0.12 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. The reaction solution was allowed to stand at 60° C. for 3 hours, at 80° C. for 3 hours, and further at 100° C. for 19 hours. The reaction was monitored by $^{19}$F-NMR. Based on the internal standard, it was confirmed that α,β,β-trifluorostyrene was obtained at a yield of 4%.

Example 7

In a glove box, a THF (0.4 mL)-C$_6$D$_6$ (0.1 mL) solution of Ni(cod)$_2$ (2.8 mg, 0.01 mmol), PCy$_3$ (5.6 mg, 0.02 mmol), 5,5-dimethyl-2-phenyl-1,3,2-dioxaborinane (19.0 mg, 0.1 mmol), and cesium carbonate (35.8 mg, 0.11 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 44%.

Example 8

In a glove box, a THF (0.4 mL)-C$_6$D$_6$ (0.1 mL) solution of Ni(cod)$_2$ (2.8 mg, 0.01 mmol), PCy$_3$ (2.8 mg, 0.01 mmol), 5,5-dimethyl-2-phenyl-1,3,2-dioxaborinane (19.0 mg, 0.1 mmol), and cesium carbonate (35.8 mg, 0.11 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 41%.

Example 9

In a glove box, a THF (0.4 mL)-C$_6$D$_6$ (0.1 mL) solution of Ni(cod)$_2$ (2.8 mg, 0.01 mmol), PCy$_3$ (2.8 mg, 0.01 mmol), 5,5-dimethyl-2-phenyl-1,3,2-dioxaborinane (19.0 mg, 0.1 mmol), and cesium carbonate (13.2 mg, 0.04 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 35%.

Example 10

In a glove box, a THF (0.4 mL)-C$_6$D$_6$ (0.1 mL) solution of Ni(cod)$_2$ (2.8 mg, 0.01 mmol), PCy$_3$ (5.6 mg, 0.02 mmol), 5,5-dimethyl-2-phenyl-1,3,2-dioxaborinane (19.0 mg, 0.1 mmol), and cesium carbonate (6.6 mg, 0.02 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 31%.

Example 11

In a glove box, a THF (0.4 mL)-C$_6$D$_6$ (0.1 mL) solution of Ni(cod)$_2$ (2.8 mg, 0.01 mmol), PCy$_3$ (2.8 mg, 0.01 mmol), 5,5-dimethyl-2-phenyl-1,3,2-dioxaborinane (19.0 mg, 0.1 mmol), and cesium carbonate (3.3 mg, 0.01 mmol) was prepared in a pressure tube (capacity: 2 mL) under an inert atmosphere. α,α,α-Trifluorotoluene (14 µL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 31%.

Example 12

In a glove box, a THF (0.4 mL)-C$_6$D$_6$ (0.1 mL) solution of Ni(cod)$_2$ (2.8 mg, 0.01 mmol), PCy$_3$ (5.6 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (14 µL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 5%.

Example 13

In a glove box, a THF (0.4 mL)-C$_6$D$_6$ (0.1 mL) solution of Ni(cod)$_2$ (2.8 mg, 0.01 mmol), PCy$_3$ (5.6 mg, 0.02 mmol), phenylboronic acid (12.2 mg, 0.1 mmol), and cesium carbonate (35.8 mg, 0.11 mmol) was prepared in a pressure tube (capacity: 2 mL) under an inert atmosphere. α,α,α-Trifluorotoluene (14 µL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 3 hours. The reaction was monitored by $^{19}$F-NMR. Based on the internal standard, it was confirmed that α,β,β-trifluorostyrene was obtained at a yield of 3%.

Example 14

In a glove box, a THF (0.4 mL)-C$_6$D$_6$ (0.1 mL) solution of Ni(cod)$_2$ (2.8 mg, 0.01 mmol), PCy$_3$ (5.6 mg, 0.02 mmol), 2-naphthaleneboronic acid (17.2 mg, 0.1 mmol), and cesium carbonate (35.8 mg, 0.11 mmol) was prepared in a pressure tube (capacity: 2 mL) under an inert atmosphere. α,α,α-Trifluorotoluene (14 µL, 0.114 mmol: internal standard for the $^{19}$F-NMR measurement) was added thereto.

TFE (0313 mmol: calculated from the container capacity described above and the applied pressure of 035 MPa) was further added thereto. This reaction solution was allowed to stand at 100° C. for 3 hours. The reaction was monitored by $^{19}$F-NMR. Based on the internal standard, it was confirmed that 2-(1,2,2-trifluorovinyl)naphthalene was obtained at a yield of 29%.

2-(1,2,2-trifluorovinyl)naphthalene $^{19}$F-NMR(C$_6$D$_6$): δ −103.29 (dd, J=71.5, 26.3 Hz, 1F), −118.00 (dd, J=71.5, 105.4 Hz, 1F) −178.56 (dd, J=105.4, 26.3 Hz, 1F), Example 15

In a glove box, a THF (0.4 mL)-THF-D$_8$ (0.1 mL) solution of Pd$_2$(dba)$_3$ (5 mg, 0.005 mmol), PCy$_3$ (5.6 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 µL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that α,β,β-trifluorostyrene was obtained at a yield of 65%.

Example 16

In a glove box, a C$_6$D$_6$ (0.5 mL) solution of Pd$_2$(dba)$_3$ (5 mg, 0.005 mmol), PCy$_3$ (5.6 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 µL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 47%.

Example 17

In a glove box, a 1,4-dioxane (0.5 mL) solution of Pd$_2$(dba)$_3$ (5 mg, 0.005 mmol), PCy$_3$ (5.6 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 µL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that α,β,β-trifluorostyrene was obtained at a yield of 54%.

Example 18

In a glove box, a CD$_3$CN (0.5 mL) solution of Pd$_2$(dba)$_3$ (5 mg, 0.005 mmol), PCy$_3$ (5.6 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 µL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that α,β,β-trifluorostyrene was obtained at a yield of 9%.

Example 19

In a glove box, a THF (0.4 mL)-THF-D$_8$ (0.1 mL) solution of Pd$_2$(dba)$_3$ (5 mg, 0.005 mmol), P(t-Bu)$_3$ (4.0 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that α,β,β-trifluorostyrene was obtained at a yield of 17%.

Example 20

In a glove box, a THF (0.4 mL)-THF-D$_8$ (0.1 mL) solution of Pd$_2$(dba)$_3$ (5 mg, 0.005 mmol), P(n-Bu)$_3$ (4.1 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that α,β,β-trifluorostyrene was obtained at a yield of 44%.

Example 21

In a glove box, a THF (0.4 mL)-THF-D$_8$ (0.1 mL) solution of Pd$_2$(dba)$_3$ (5 mg, 0.005 mmol), ethylenebis (biscyclohexylphosphine) (P(Cy)$_2$CH$_2$CH$_2$P(Cy)$_2$) (8.5 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that, α,β,β-trifluorostyrene was obtained at a yield of 42%.

Example 22

In a glove box, a THF (0.4 mL)-THF-D$_8$ (0.1 mL) solution of Pd$_2$(dba)$_3$ (5 mg, 0.005 mmol), P(o-tol)$_3$ (6.1 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that α,β,β-trifluorostyrene was obtained at a yield of 21%.

Example 23

In a glove box, a THF (0.4 mL)-THF-D$_8$ (0.1 mL) solution of Pd$_2$(dba)$_3$ (5 mg, 0.005 mmol), Pt-Bu$_2$Me (3.2 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was, confirmed that α,β,β-trifluorostyrene was obtained at a yield of 60%.

Example 24

In a glove box, a THF (0.4 mL)-THF-D$_8$ (0.1 mL) solution of Pd$_2$(dba)$_3$ (5 mg, 0.005 mmol), PCy$_3$ (5.6 mg, 0.02 mmol), phenylboronic acid pinacol ester (20.4 mg, 0.1 mmol), and cesium carbonate (39.1 mg, 0.12 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 18%.

Example 25

In a glove box, a THF (0.4 mL)-THF-D$_8$ (0.1 mL) solution of Pd$_2$(dba)$_3$ (5 mg, 0.005 mmol), PCy$_3$ (5.6 mg, 0.02 mmol), phenylboronic acid (12.2 mg, 0.1 mmol), and cesium carbonate (39.1 mg, 0.12 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 2 hours. The reaction was monitored by $^{19}$F-NMR. Based on the internal standard, it was confirmed that α,β,β-trifluorostyrene was obtained at a yield of 19%.

Example 26

In a glove box, a THF (0.4 mL)-THF-D$_8$ (0.1 mL) solution of Pd$_2$(dba)$_3$ (5 mg, 0.005 mmol), PCy$_3$ (5.6 mg, 0.02 mmol), 2-naphthylboronic acid (17.2 mg, 0.1 mmol), and cesium carbonate (39.1 mg, 0.12 mmol) was prepared in a pressure tube (capacity: 2 mL) under an inert atmosphere. α,α,α-Trifluorotoluene (14 μL, 0.114 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 2 hours. The reaction was monitored by $^{19}$F-NMR. Based on the internal standard, it was confirmed that 2-(1,2,2-trifluoroethenyl)naphthalene was obtained at a yield of 44%.

2-(1,2,2-Trifluoroethenyl)naphthalene $^{19}$F-NMR (THF-d$_8$, δ/ppm): −178.4 (dd, J$_{FF}$=32.0, 108.8 Hz, 1F), −118.0 (dd, J$_{FF}$=72.3, 108.8 Hz, 1F), −103.4 (dd, J$_{FF}$=31.0, 72.3 Hz, 1F).

Example 27

In a glove box, a THF (0.4 mL)/C$_6$D$_6$ (0.1 mL) solution of Ni(cod)$_2$ (2.8 mg, 0.01 mmol), P(n-Bu)$_3$ (4.1 mg, 0.02 mmol), 5,5-dimethyl-2-phenyl-1,3,2-dioxaborinane (19.0 mg, 0.1 mmol), and cesium carbonate (39.1 mg, 0.12 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 27%.

Example 28

In a glove box, a THF (0.4 mL)/C$_6$D$_6$ (0.1 mL) solution of Ni(cod)$_2$ (2.8 mg, 0.01 mmol), P(t-Bu)$_3$ (4.0 mg, 0.02 mmol), 5,5-dimethyl-2-phenyl-1,3,2-dioxaborinane (19.0 mg, 0.1 mmol), and cesium carbonate (39.1 mg, 0.12 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 15%.

Example 29

In a glove box, a THF (0.4 mL)-THF-D$_8$ (0.1 mL) solution of Pd$_2$(dba)$_3$ (5 mg, 0.005 mmol), PCy$_3$ (5.6 mg, 0.02 mmol), and 2-(2-naphthyl)-5,5-dimethyl-1,3,2-dioxaborinane (24.0 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that 2-(1,2,2-trifluoroethenyl)naphthalene was obtained at a yield of 67%.

Example 30

In a glove box, a THF (0.4 mL)-THF-D$_8$ (0.1 mL) solution of Pd$_2$(dba)$_3$ (5 mg, 0.005 mmol), PCy$_3$ (5.6 mg, 0.02 mmol), and 5,5-dimethyl-2-[4-(trifluoromethyl)phenyl]-1,3,2-dioxaborinane (25.8 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that 1-(1,2,2-trifluoroethenyl)-4-(trifluoromethyl)benzene was obtained at a yield of 50%.

1-(1,2,2-Trifluoroethenyl)-4-(trifluoromethyl)benzene $^{19}$F-NMR (THF-d$_8$, δ/ppm): −179.8 (dd, J$_{FF}$=32.8, 109.2 Hz, 1F), −115.0 (dd, J$_{FF}$=65.5, 109.2 Hz, 1F), −100.8 (dd, J$_{FF}$=32.6, 65.1 Hz, 1F), −65.5 (s, 3F).

Example 31

In a glove box, a THF (0.4 mL)-THF-D$_8$ (0.1 mL) solution of Pd$_2$(dba)$_3$ (5 mg, 0.005 mmol), PCy$_3$ (5.6 mg, 0.02 mmol), and 5,5-dimethyl-2-(4-formyl)phenyl-1,3,2-dioxaborinane (21.8 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that 1-(1,2,2-trifluoroethenyl)-4-(formyl)benzene was obtained at a yield of 41%.

1-(1,2,2-Trifluoroethenyl)-4-(formyl)benzene $^{19}$F NMR (376 MHz, THF-d$_8$, d/ppm): −180.0 (dd, J$_{FF}$=32.8, 108.4 Hz, 1F), −114.3 (dd, J$_{FF}$=63.5, 108.4 Hz, 1F), −100.4 (dd, J$_{FF}$=32.8, 63.5 Hz, 1F)

Example 32

In a glove box, a THF (0.4 mL)-THF-D$_8$ (0.1 mL) solution of Pd$_2$(dba)$_3$ (5 mg, 0.005 mmol), PCy$_3$ (5.6 mg, 0.02 mmol), and 1,4-bis-(5,5-dimethyl-1,3,2-dioxaborinan-2-yl)benzene (30.2 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that 1,4-bis-(1,2,2-trifluoroethenyl)benzene was obtained at a yield of 10% and 1-(5,5-dimethyl-1,3,2-dioxaborinan-2-yl)-4-(1,2,2-trifluoroethenyl)benzene was obtained at a yield of 25%.

1,4-bis-(1,2,2-Trifluoroethenyl)benzene $^{19}$F-NMR (THF-d$_8$, δ/ppm): −178.4 (dd, J$_{FF}$=33.0, 108.0 Hz, 1F), −114.3 (dd, J$_{FF}$=70.0, 108.0 Hz, 1F), −87.9 (dd, J$_{FF}$=33.0, 70.0 Hz, 1F 1-(5,5-Dimethyl-1,3,2-dioxaborinan-2-yl)-4-(1,2,2-trifluoroethenyl)benzene $^{19}$F NMR (376 MHz, THF-d$_8$, d/ppm): −179.7 (dd, J$_{FF}$=32.4, 108.9 Hz, 1F), −117.4 (dd, J$_{FF}$=71.2, 108.9 Hz, 1F), −103.4 (dd, J$_{FF}$=32.4, 71.2 Hz, 1F)

Example 33

In a glove box, a THF (0.4 mL)-THF-D$_8$ (0.1 mL) solution of Pd$_2$(dba)$_3$ (5 mg, 0.005 mmol), PCy$_3$ (5.6 mg, 0.02 mmol), and 1,4-bis-(5,5-dimethyl-1,3,2-dioxaborinan-2-yl)benzene (30.2 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 60 hours. The reaction was monitored by $^{19}$F-NMR. Based on the internal standard, it was confirmed that 1,4-bis-(1,2,2-trifluoroethenyl)benzene was obtained at a yield of 32%.

Example 34

In a glove box, a THF (0.4 mL)-THF-$D_8$ (0.1 mL) solution of $Pd_2(dba)_3$ (5 mg, 0.005 mmol), $PCy_3$ (5.6 mg, 0.02 mmol), and 5,5-dimethyl-2-(4-methoxycarbonyl)phenyl-1,3,2-dioxaborinane (24.8 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that 1-(methoxycarbonyl)-4-(1,2,2-trifluoroethenyl)benzene was obtained at a yield of 38%.

1-(Methoxycarbonyl)-4-(1,2,2-trifluoroethenyl)benzene $^{19}$F NMR (376 MHz, THF-$d_8$, d/ppm): −180.1 (dd, $J_{FF}$=32.8, 108.8 Hz, 1F), −115.0 (dd, $J_{FF}$=65.6, 108.8 Hz, 1F), −101.2 (dd, $J_{FF}$=32.8, 65.6 Hz, 1F)

Example 35

In a glove box, a THF (0.4 mL)-THF-$D_8$ (0.1 mL) solution of $Pd_2(dba)_3$ (5 mg, 0.005 mmol), $PCy_3$ (5.6 mg, 0.02 mmol), and 5,5-dimethyl-2-(4-cyano)phenyl-1,3,2-dioxaborinane (20.4 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto.

TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that 4-(1,2,2-trifluoroethenyl)benzonitrile was obtained at a yield of 25%.

4-(1,2,2-Trifluoroethenyl)benzonitrile $^{19}$F NMR (376 MHz, THF-$d_8$, d/PPm): −180.6 (dd, $J_{FF}$=32.7, 108.4 Hz, 1F), −113.6 (dd, $J_{FF}$=63.4, 108.4 Hz, 1F), −99.5 (dd, $J_{FF}$=32.7, 63.4 Hz, 1F)

Example 36

In a glove box, a THF (0.4 mL)-THF-$D_8$ (0.1 mL) solution of $Pd_2(dba)_3$ (5 mg, 0.005 mmol), $PCy_3$ (5.6 mg, 0.02 mmol), and 2-(5,5-dimethyl-1,3,2-dioxaborinan-2-yl)toluene (21.5 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 5 hours. The reaction was monitored by $^{19}$F-NMR. Based on the internal standard, it was confirmed that 2-(1,2,2-trifluoroethenyl)toluene was obtained at a yield of 50%.

2-(1,2,2-Trifluoroethenyl)toluene $^{19}$F-NMR (THF-$d_8$, δ/ppm): −163.8 (dd, $J_{FF}$=29.4, 117.1 Hz, 1F), =121.4 (dd, $J_{FF}$=77.6, 117.1 Hz, 1F), −107.1 (dd, $J_{FF}$=29.4, 77.6 Hz, 1F Example 37

In a glove box, a THF (0.4 mL)-THF-$D_8$ (0.1 mL) solution of $Pd_2(dba)_3$ (5 mg, 0.005 mmol), $PCy_3$ (5.6 mg, 0.02 mmol), and 5,5-dimethyl-2-phenyl-1,3,2-dioxaborinane (19.0 mg, 0.1 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. Hexafluoropropene (HFP) (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that (Z)-1-phenyl-1,2,3,3,3-pentafluoro-1-propene was obtained at a yield of 48%, (E)-1-phenyl-1,2,3,3,3-pentafluoro-1-propene was obtained at a yield of 10%, and 2-phenyl-1,1,3,3,3-pentafluoro-1-propene was obtained at a yield of 10%.

(Z)-1-Phenyl-1,2,3,3,3-pentafluoro-1-propene $^{19}$F-NMR (THF-$d_8$, δ/ppm): −158.7 (qd, $J_{FF}$=12.6, 9.3 Hz, 1F), −110.5 (qd, $J_{FF}$=8.2, 9.3 Hz, 1F), −68.5 (dd, $J_{FF}$=12.6, 8.2 Hz, 3F).

(E)-1-Phenyl-1,2,3,3,3-pentafluoro-1-propene $^{19}$F-NMR (THF-$d_8$, δ/ppm): −173.1 (qd, $J_{FF}$=10.4, 130.9 Hz, 1F), −148.1 (qd, $J_{FF}$=21.9, 130.9 Hz, 1F), −69.8 (dd, $J_{FF}$=21.9, 10.4 Hz, 3F).

2-Phenyl-1,1,3,3,3-pentafluoro-1-propene $^{19}$F-NMR (THF-$d_8$, δ/ppm): −80.6 (qd, $J_{FF}$=10.9, 14.9 Hz, 1F), −79.4 (qd, $J_{FF}$=23.4, 14.9 Hz, 1F), −62.0 (dd, $J_{FF}$=23.4, 10.9 Hz, 3F).

Example 38

In a glove box, a THF (0.4 mL)/$C_6D_6$ (0.1 mL) solution of $Ni(cod)_2$ (2.8 mg, 0.01 mmol), $PPh_3$ (5.3 mg, 0.02 mmol), 5,5-dimethyl-2-phenyl-1,3,2-dioxaborinane (19.0 mg, 0.1 mmol), and cesium carbonate (39.1 mg, 0.12 mmol) was prepared in a pressure tube (capacity: 2 mL) under an inert atmosphere. α,α,α-Trifluorotoluene (12 μL, 0.097 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 100° C. for 20 hours. The reaction was monitored by $^{19}$F-NMR. Based on the internal standard, it was confirmed that α,β,β-trifluorostyrene was obtained at a yield of 14%.

Reference Example 1

In a glove box, a THF (0.4 mL)-THF-$d_8$ (0.1 mL) solution of Ni ($η^2$-TFE) $(PCy_3)_2$ (28.8 mg, 0.04 mmol), COD (4.9 μL, 0.04 mmol), and 5,5-dimethyl-2-phenyl-1,3,2-dioxaborinane (7.6 mg, 0.04 mmol) was prepared in a pressure tube (capacity: 2 mL) under an inert atmosphere. α,α,α-Trifluorotoluene (12.3 μL, 0.100 mmol: internal standard for the $^{19}$F-NMR measurement) was added thereto. TFE (0.313 mmol: calculated from the container capacity described above and the applied pressure of 0.35 MPa) was further added thereto. This reaction solution was allowed to stand at 60° C. for 3 hours and further at 80° C. for 72 hours. The reaction was monitored by $^{19}$F-NMR. Based on the internal standard, it was confirmed that 1,1-difluoro-2,2-diphenylethylene was obtained at a yield of 10%.

INDUSTRIAL APPLICABILITY

The present invention makes it possible to produce a fluorine-containing olefin substituted with an organic group or groups easily and efficiently (high yield, high selectivity, and low cost).

The invention claimed is:

1. A method for preparing a fluorine-containing olefin substituted with an organic group or groups,
   the method comprising a step of reacting a fluorine-containing olefin, which is an olefin substituted with one or more fluorine atoms and at least one of the fluorine atoms is bonded to an sp$^2$ hybridized carbon atom, with an organic boron compound in the presence of an organic transition metal catalyst containing at least one transition metal selected from the group consisting of nickel, palladium, platinum, rhodium, ruthenium, and cobalt,
   to replace at least one fluorine atom bonded to the sp$^2$ hybridized carbon atom with a group represented by R,
   wherein R is an optionally substituted aryl, an optionally substituted heteroaryl that is bonded via a carbon atom thereof, an optionally substituted cycloalkyl, an optionally substituted alkyl, an optionally substituted alkenyl, or an optionally substituted alkynyl.

2. The method according to claim 1, wherein the fluorine-containing olefin is one or more members selected from the group consisting of tetrafluoroethylene, hexafluoropropylene, trifluoroethylene, 1,1-difluoroethylene, and 1,2-difluoroethylene.

3. The method according to claim 1, wherein the transition metal is at least one member selected from the group consisting of nickel and palladium.

4. The method according to claim 1, wherein the organic boron compound is represented by Formula (1):

  (1)

wherein R is the same as defined in claim 1;
Y is a hydroxy group, an alkoxy group, or an alkyl group; and
two alkoxy or alkyl groups represented by two Ys may be crosslinked to each other; or
the organic boron compound is represented by Formula (1'):

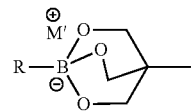

wherein M' is lithium metal, sodium metal, or potassium metal.

5. The method according to claim 4, wherein R is an optionally substituted monocyclic, bicyclic, or tricyclic aryl.

6. The method according to claim 1, wherein the step is performed in the presence of a base.

7. The method according to claim 1, wherein the step is performed in the absence of a base.

8. The method according to claim 1, wherein the organic transition metal catalyst is an organic nickel complex.

9. The method according to claim 1, wherein the organic transition metal catalyst is an organic palladium complex.

10. The method according to claim 1, wherein the fluorine-containing olefin substituted with an organic group or groups is a compound represented by Formula (2):

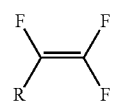

the same as defined in claim 1.

11. A compound represented by Formula (2a):

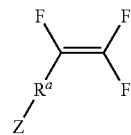

wherein R$^a$ is an optionally substituted allylene or an optionally substituted heteroallylene,
Z is a group represented by Formula: —BY$_2$, wherein Y is a hydroxy group, an alkoxy group, or an alkyl group; and
two alkoxy or alkyl groups represented by two Ys may be crosslinked to each other; or
Formula:

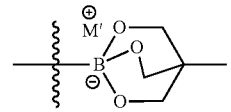

wherein M' is lithium metal, sodium metal, or potassium metal.

* * * * *